(12) United States Patent
Khan et al.

(10) Patent No.: US 8,024,913 B2
(45) Date of Patent: Sep. 27, 2011

(54) PREPARED MEDICATION BAGGING SYSTEM AND METHOD

(75) Inventors: Abdul Wahid Khan, Lindenhurst, IL (US); Dennis Tribble, Ormond Beach, FL (US); Edward Lefebre, Port Orange, FL (US); Jim Shafer, Deland, FL (US)

(73) Assignee: FHT, Inc., Daytona Beach, FL (US)

( * ) Notice: Subject to any disclaimer, the term of this patent is extended or adjusted under 35 U.S.C. 154(b) by 379 days.

(21) Appl. No.: 12/327,412

(22) Filed: Dec. 3, 2008

(65) Prior Publication Data

US 2010/0107570 A1 May 6, 2010

Related U.S. Application Data

(60) Provisional application No. 61/109,768, filed on Oct. 30, 2008.

(51) Int. Cl.
*B65B 39/06* (2006.01)
(52) U.S. Cl. .............. 53/576; 53/469; 53/567; 53/574
(58) Field of Classification Search .............. 53/576, 53/469, 479, 510, 64, 567, 568, 570, 574
See application file for complete search history.

(56) References Cited

U.S. PATENT DOCUMENTS

| | | | | |
|---|---|---|---|---|
| 4,110,956 A | * | 9/1978 | Weisberg | 53/558 |
| 4,180,297 A | * | 12/1979 | Abrams | 312/406 |
| 4,336,632 A | * | 6/1982 | Wilson et al. | 452/25 |
| 4,590,748 A | * | 5/1986 | Harrison et al. | 53/576 |
| 5,524,413 A | * | 6/1996 | Fukuda | 53/64 |
| 6,216,425 B1 | * | 4/2001 | Hanten | 53/450 |
| 6,915,823 B2 | | 7/2005 | Osborne | |
| 7,017,622 B2 | | 3/2006 | Osborne | |
| 7,055,717 B1 | * | 6/2006 | Koh | 221/294 |
| 7,117,902 B2 | | 10/2006 | Osborne | |
| 7,484,292 B2 | * | 2/2009 | Bussey et al. | 29/728 |
| 2004/0016098 A1 | | 1/2004 | Reich | |

FOREIGN PATENT DOCUMENTS

| | | |
|---|---|---|
| JP | 2007-014610 | 1/2007 |
| KR | 10-2002-0004505 | 1/2002 |
| KR | 20-0384581 | 5/2005 |

* cited by examiner

*Primary Examiner* — Christopher Harmon
(74) *Attorney, Agent, or Firm* — Leason Ellis LLP

(57) ABSTRACT

An apparatus for sealing prepared medications in enclosures includes a tubular sleeve having an open first end, an open second end, and an outer surface. The first end includes at least one first locking member for securely attaching the tubular sleeve to another member. The apparatus also includes a length of a flexible packaging sleeve that is open at one end and has an open interior space. The packaging sleeve is disposed about the outer surface of the tubular sleeve in a compressed form. The open end of the sleeve is sealingly attached to the first end of the tubular sleeve. A tensioner device is disposed about an outer surface of the packaging sleeve and includes a first section that couples the first end of the packaging sleeve to the tubular sleeve and at least two elongated tensioner arms that extend along a length of the tubular sleeve. The compressed packaging sleeve is disposed underneath the tensioner arms such that the tensioner arms apply tension to the packaging sleeve and control the unfurling thereof from the tubular sleeve. The open first end of the tubular sleeve is in communication with the open interior space of the packaging sleeve.

9 Claims, 11 Drawing Sheets

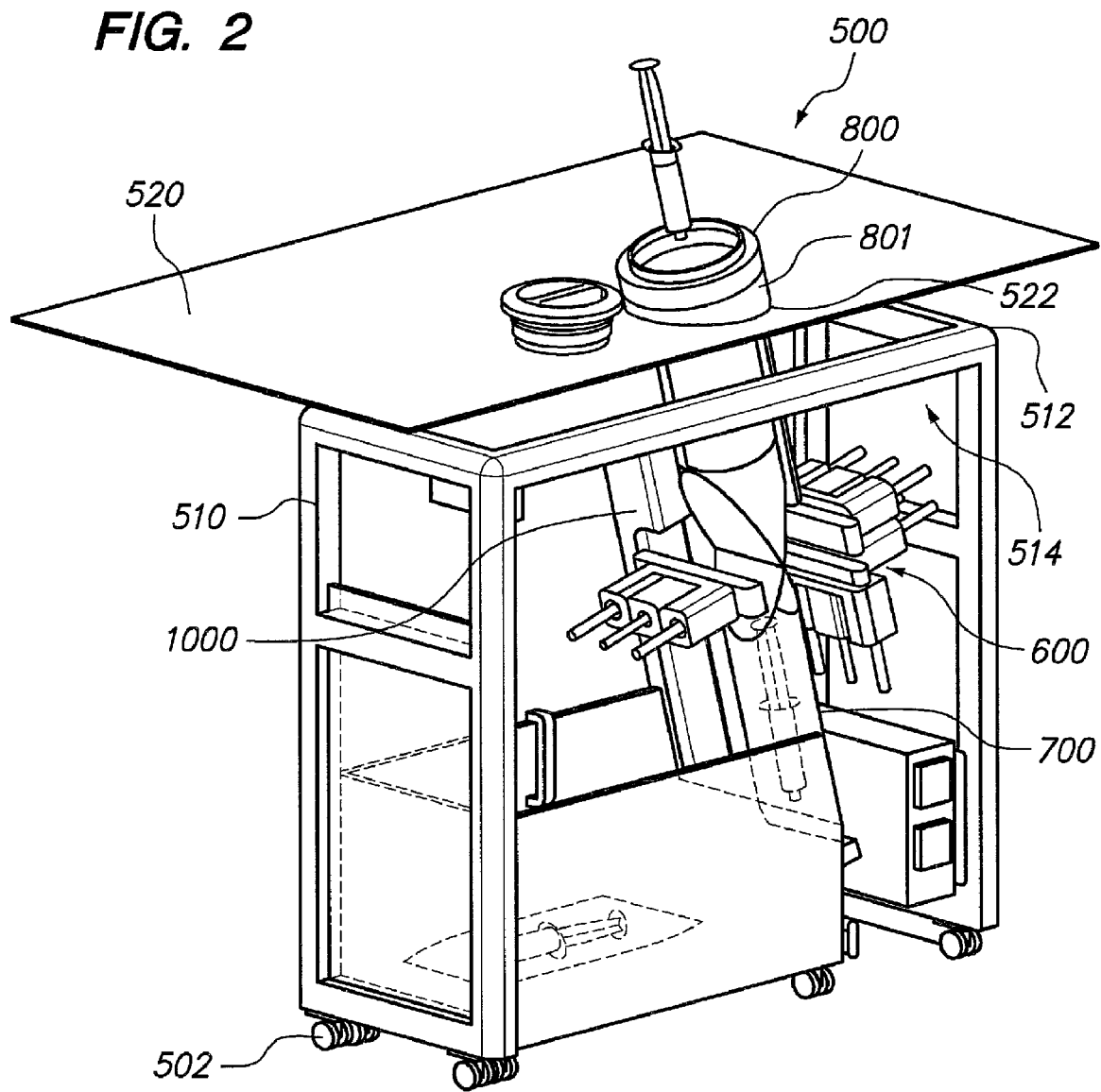

PREPARED MEDICATION BAGGING SYSTEM AND METHOD

CROSS-REFERENCE TO RELATED APPLICATION

The present application claims the benefit of U.S. patent application Ser. No. 61/109,768, filed Oct. 30, 2008, which is hereby incorporated by reference in its entirety.

TECHNICAL FIELD

The present invention relates generally to a handling system that seals items individually so as to prevent operator exposure to the item and in particular, to medical and pharmaceutical equipment including a bag handling system that receives items, such as IV bags, syringes, etc., in a controlled environment and individually seals each item in a package (enclosure) while maintaining the sterile environment.

BACKGROUND

There are a vast amount of different types of drugs that come in different forms and are designed to treat a wide range of conditions and illnesses and diseases. One of the more deadly and unfortunately common diseases is cancer. Cancer is a class of diseases in which a group of cells displays uncontrolled growth, which is cell division beyond the normal limits; invasion, which is where cells intrude on and destroy adjacent tissues, and metastasis, which is where cells spread to other locations in the body via lympth or blood. Many cancers can be treated and even some can be cured, depending upon a number of factors, such as the type of cancer, the location and the stage of the cancer. Once diagnosed, cancer is usually treated with a combination of surgery, chemotherapy and radiotherapy. Chemotherapy is the treatment of cancer with drugs that can destroy cancer cells.

One class of chemotherapy drugs is antineoplastics, also known as cytotoxic antibiotics, which are drugs that inhibit and combat development of tumors. Cytotoxic drugs are toxic compounds that are known to have carcinogenic, mutagenic and/or teratogenic potential. With direct contact, these compounds can cause irritation to the skin, eyes, and mucous membranes and ulceration and necrosis of tissue. As a result of the high level of toxicity of these drugs, the exposure of health-care personnel to these drugs should be minimized.

During drug preparation, a variety of manipulations and handling tasks are performed which can result in aerosol generation, spraying, and splattering of the drug. Some of the more common manipulations include but are not limited to: the withdrawal of needles from drug vials, the use of syringes and needles for drug transfer or drug reconstitution, and the expulsion of air from the syringe when measuring the precise volume of a drug. The contamination may be a direct transfer of the drug to the body of the health-care provider or the exterior of the medical product, such as a syringe or IV bag can be contaminated with the drug and then later transferred by direct contact between a person and the contaminated exterior surface.

Pharmaceutical practice calls for the use of aseptic techniques and a sterile environment. Many pharmacies attempt to provide this sterile environment by using a horizontal laminar flow work bench. While this type of equipment provides some benefit, it suffers from a number of shortcomings, including that it can expose the operator and other health-care personnel or others in the same room to aerosols generated during drug preparation procedures. As a result of this concern, a Class 11 laminar flow (vertical) biological safety cabinet (with HEPA filter) that is designed to provide both product and operator protection is needed when dealing with and handling cytotoxic drugs. Syringes and unclipped needles can be disposed of by manually placing these items into leakproof containers.

The disposal of cytotoxic drugs and trace contaminated materials (e.g., gloves, gowns, needles, syringes, vials, etc.) presents a possible source of exposure to pharmacists, nurses, and physicians, as well as to other staff members, including the cleaning and janitorial staff.

The adverse health effects associated with antineoplastic agents (cancer chemotherapy drugs, cytotoxic drugs) in cancer patients and some non-cancer patients treated with these drugs are well-documented. The very nature of antineoplastic agents makes them harmful to healthy constantly dividing cells and tissues, as well as the cancerous cells. For cancer patients with a life-threatening disease, there is a great benefit to treatment with these agents. However, for the healthcare personnel that are exposed to antineoplastic agents as part of their work practice, precautions should be taken to eliminate or reduce exposure as much as possible. There already is a limitation in cytotoxics dissolution in Australia and the United States to 20 dissolutions per pharmacist/nurse, since pharmacists that prepare these drugs or nurses that may prepare and/or administer them are the two occupational groups with the highest potential exposure to antineoplastic agents. In addition, physicians and operating room personnel may also be exposed through the treatment of patients. Hospital staff, such as shipping and receiving personnel, custodial workers, laundry workers, and waste handlers, all have potential exposure to these drugs during the course of their work. The increased use of antineoplastic agents in veterinary oncology also puts these workers at risk for exposure to these drugs.

Since conventional methods for preparing and handling cytotoxin drugs are essentially very manual, labor intensive in nature, the operator performing these tasks is exposed to the hazardous side effects of the cytotoxin drugs. There is therefore a need for an improved, safer method and system for handling cytotoxin drugs particularly in drug preparation and drug transfer environments.

SUMMARY

In accordance with one embodiment, an apparatus for sealing prepared medications in enclosures includes a tubular sleeve having an open first end, an open second end, and an outer surface. The first end includes at least one first locking member for securely attaching the tubular sleeve to another member. The apparatus also includes a length of a flexible packaging sleeve that is open at one end, closed at the other end and has an open interior space. The packaging sleeve is disposed about the outer surface of the tubular sleeve in a compressed form. The open end of the sleeve is sealingly attached to the first end of the tubular sleeve. A tensioner device is disposed about an outer surface of the packaging sleeve and includes a first section that couples the first end of the packaging sleeve to the tubular sleeve and at least two elongated tensioner arms that extend along a length of the tubular sleeve. The compressed packaging sleeve is disposed underneath the tensioner arms such that the tensioner arms apply tension to the packaging sleeve and control the unfurling thereof from the tubular sleeve. The open first end of the tubular sleeve is in communication with the open interior space of the packaging sleeve.

A method for sealing a prepared medication in an enclosure includes the steps of: maintaining a first space as a controlled, sealed environment and inserting the prepared medication into an open end of a tubular sleeve that has an outer surface. The open end of the tubular sleeve is exposed to the first space and a length of a flexible packaging sleeve that is open at one end and sealed at an opposite end. The packaging sleeve has an open interior space is disposed about the outer surface of the tubular sleeve in a compressed form. The open end of the sleeve is sealingly attached to the first end of the tubular sleeve such that the prepared medication is inserted into the open interior space. The method also includes the step of unfurling a predetermined length of the packaging sleeve from the tubular sleeve. The unfurling of the packaging sleeve is metered and controlled by a tensioner device that is disposed about an outer surface of the packaging sleeve and located exterior to the compressed packaging sleeve and applies tension to the packaging sleeve. The packaging sleeve is sealed along a seal zone or area.

In another embodiment, an apparatus for sealing prepared medications in enclosures includes a frame defining a first sealed space and a tubular sleeve having an open first end that is in selective communication with the first sealed space, an open second end, and an outer surface. The apparatus also includes a length of a flexible packaging sleeve that is open at one end and has an open interior space. The packaging sleeve is disposed about the outer surface of the tubular sleeve in a compressed form. The open end of the sleeve is sealingly attached to the first end of the tubular sleeve and the apparatus further includes a tensioner device that is disposed about an outer surface of the packaging and applies tension to the packaging sleeve to control the unfurling thereof from the tubular sleeve. A sleeve locking member is coupled to the frame for releasably locking the tubular sleeve thereto the sleeve locking member when the first and second locking members engage one another. The sleeve locking member is constructed to permit the open first end of the tubular sleeve to be exposed to the sealed space. A cap that is releasably attached to the first end of the tubular sleeve for sealing the first end, wherein the cap is constructed such that it cannot be removed until the tubular sleeve and the sleeve locking member are in a locked position where the tubular sleeve is sealed relative to the first space.

These and other aspects, features and advantages shall be apparent from the accompanying Drawings and description of certain embodiments of the invention.

BRIEF DESCRIPTION OF THE DRAWINGS

FIG. 2 is a perspective view of a bag handling system for use in the handling station of FIG. 1;

DETAILED DESCRIPTION OF CERTAIN EMBODIMENTS OF THE INVENTION

Figure 1:
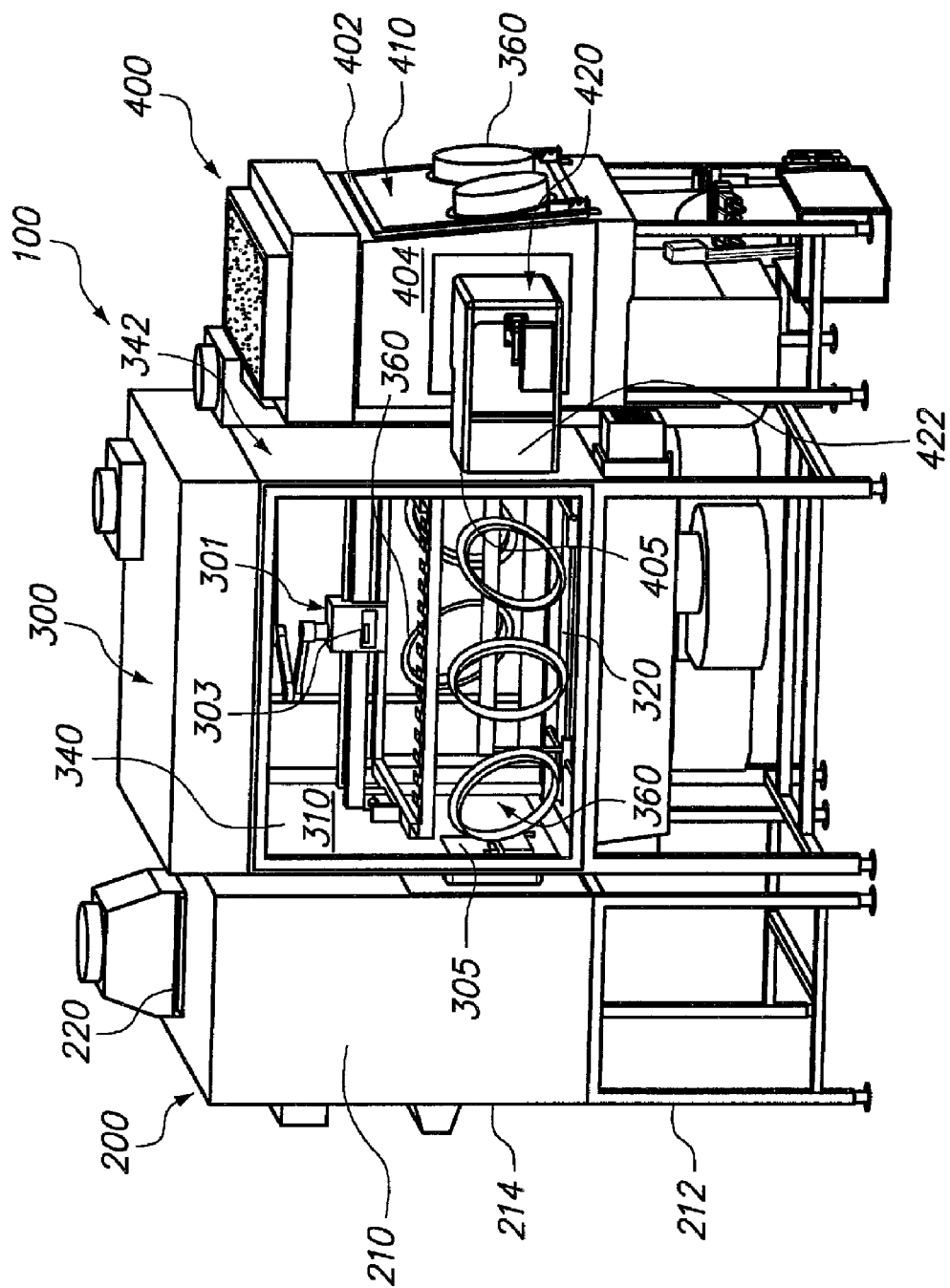
FIG. 1 is a front perspective view of a multi-stage end-to-end cytotoxin handling station according to a first embodiment of the invention.

A multi-stage end-to-end cytotoxin handling station 100 is illustrated in FIG. 1 according to one exemplary embodiment. The station 100 is designed to perform a number of operations that generally relate to the drug processing and drug transfer fields and in particular, the station 100 is configured to receive drugs and equipment in a sealed environment, such as syringes, etc.; to process and prepare drug doses in a sealed environment; and to package drug products and/or dispose of medical waste in a sealed environment.

More specifically, the station 100 includes a first section 200 for receiving drugs and medical equipment, as well as performing drug preparation, a second section 300 for processing the drugs and preparing drug doses; and a third section 400 for further processing of the doses and for sealing the doses, as well as medical equipment, in sealed enclosures that can then be transported from the station 100 to a point of use. It will be understood and as set forth in greater detail hereinafter, the operations performed in each section are conducted in a sealed, sterile environment, thereby reducing the risk of personnel being exposed to the cytotoxin drug.

The first section 200 includes a housing 210 that defines an interior chamber 220 which has a bottom surface or floor onto which items, such as drug vials, syringes, IV bags, etc., can be placed. In the illustrated embodiment, the housing 210 is a hollow rectangular structure that is supported by a set of legs 212. The interior chamber 220 is connected to a vacuum source so that the interior is maintained at a negative pressure. The housing 210 includes a means for delivering items into the interior chamber 220. For example, the housing 210 can include a sealed doorway (not shown) or the like formed along a first wall 214 that is exposed and faces away from the second section 300. The sealed doorway permits items to be placed into the negative pressure environment of the interior chamber 220.

Typically, the items, such as drug vials, syringes, etc., that are placed in the interior chamber 220 are in sealed packaging. For example, a drug vial containing a cytotoxin drug, is typically sealed in protective plastic packaging so as to provide a barrier between the vial and the operator. Similarly, the medical equipment, such as syringes and the like, are sealed in packaging. Items that are needed to prepare a medication dose are thus introduced into the interior chamber 220.

The first section 200 can include automated equipment that is used for drug preparation. For example, the automated equipment can include a robotic device that receives loaded items and transports them from one location to another location within the interior chamber 220. The robotic device is configured so that it can receive any number of different sized and shaped items, including drug vials, syringes, IV bags, etc. The automated equipment can also include an automated drug preparation device that is configured to perform a number of drug preparation steps, including removal of a cap from the drug vial, reconstituting the medication, withdrawing (aspirating) the contents of the drug vial, etc. Applicants' previous patents, e.g., U.S. Pat. Nos. 7,117,902; 6,915,823; 7,017,622, etc., generally describe certain components that can be utilized in the first section 220.

In one embodiment, once the drug dose has been properly prepared in the first section 200, it can be grouped with other drug doses and/or other medical equipment, and placed on a substrate, such as a tray or the like, thereby defining a kit that can be transported to a point of use location.

The first section 200 is in selective fluid communication with the second section 300 to allow the controlled movement of items from the first section 200 to the second section 300. For example, an internal pass through or door 305 can be formed in the common wall between the first and second sections 200, 300 or within the adjacent walls of the first and second section 200, 300 that face one another. In the closed position, the first and second sections 200, 300 are sealed from one another.

The second section 300 is defined by a hollow body (rectangular or square shaped) that defines an interior chamber 310. The second section 300 includes a bottom wall or floor 320 onto which items can be placed and can include a set of legs that support the bottom wall 320. The illustrated section 300 also includes a pair of side walls 330 that are formed of a transparent material to allow an operator to view the inside (interior chamber 310) of the second section 300. Opposite ends walls 340, 342 of the second section 300 face the first and third sections 200, 400, respectively. The pass through or door 305 is formed in end wall 340.

As with the first section 200, the second section 300 is operatively coupled to a vacuum source and therefore, the interior chamber 310 thereof operates in vacuum conditions. This permits the operator to perform operations in the interior chamber 310 in a controlled environment.

The second section 300 also includes a plurality of sealed glove ports 360 formed in the side walls 330 to allow an operator to physically and manually manipulate (pickup, move, etc.) items that are present in the interior chamber 310. For example, one side wall (the front of the second section 300) can include three glove ports 360, while the other side wall (the back of the second section 300) can include two glove ports 360. Gloves, such as thick rubber gloves are sealingly attached to the glove ports 360 to allow an operator to insert his or hand therein and touch items that are located in the interior chamber 310. At least of the glove ports 360 and attached glove is located near the door 305 so that the operator can open the door 305 using the glove and retrieve items from the first section 200. It will be appreciated that the glove ports 360 can be arranged at different heights within the interior chamber 310.

It will be appreciated that while the drug processing steps that are undertaken in the second section (second stage) 300 can be done manually, the second section 300 can include an automated dose preparation system, such as the one indicated at 301. The automated dose preparation system 301 can be similar to the ones disclosed in Applicant's patents listed and referenced herein. For example, the system 301 is a computer based system that allows the user to input instructions and a robotic device, such as the one shown at 303, operates to retrieve the items from the first section 200 and then performs processing operations in the second section 300. For example, the robotic device 303 can retrieve syringes, IV bags, or the like from the first section 200 and then further process these components in the second section before delivering the components to the third section 400 in an automated manner, while maintaining the controlled environment.

Similar to the interface between the first section 200 and the second section 300, the second section 300 is in selective communication with the third section 400. As with the first and second sections 200, 300, the third section 400 is a hollow body that has an interior chamber 410 and a set of legs which support the body. As with the first and second sections 200, 300, the third section 400 is operatively connected to a vacuum source and therefore, the interior chamber 410 is under negative pressure.

One end of the third section 400 faces the second section 300, while an opposite end defines an exposed end 402. The third section 400 also includes side walls 404. There can be a common wall between the second section 300 and the third section 400 or the sections can have respective walls that abut one another.

An internal pass through or door 405 provides selective communication between interior chamber 310 and interior chamber 410 and in the illustrated embodiment, the door 405 is located outside of the interior chamber 410. For example, a manifold 420 or the like is sealingly coupled to the door 405 at one end 422, while an opposite end 424 is sealingly coupled to one side wall 404. The door 405 thus sealingly closes off the manifold 420 to the interior chamber 310 and vice versa. At the end 424, a pivotable flap (rubber flap) (not shown) is provided to cover the opening formed in the side wall 404. In a rest position, the flap is in the closed position and closes off the manifold 420 from the interior chamber 410. In addition, the manifold 420 includes an exterior door (not shown) that is formed along one side wall thereof between the ends 422, 424. The door sealingly closes with respect to the manifold 420 to maintain the interior of the manifold 420 as a controlled environment under negative pressure. However, when opened, the door permit the operator to retrieve items located in the interior of the manifold 420.

The manifold 420 permits items, such as prepared doses, to be passed from the second section 300 to the third section 400 in a sterile, controlled environment. Exposed end 402 can be a transparent wall and includes a pair of glove ports 360 to permit the operator to manipulate items that are contained within the interior chamber 410. One of the glove ports 360 is located proximate the flap to allow the operator to have access to the interior of the manifold.

In contrast to the first and second sections 200, 300, the third section 400 does not include a bottom wall or floor but instead is open at least in several different locations (e.g., one or more rectangular openings). The opening(s) is designed to receive the bag handling system 500 that is illustrated in FIG. 2. As described below in detail, the bag handling system 500 is configured to receive an item in the sealed, controlled environment of the interior chamber 410 and allow each item to the sealingly closed in an individual enclosure in an least partially automated manner.

The bag handling system 500 can be a portable system and therefore, can include wheels 502 to permit the system 500 to be easily moved from one location to another location. The system 500 is defined by a frame 510 (e.g., a cart shaped frame). The frame 510 has an open top portion 512 that supports a substrate (countertop) 520. As illustrated, one exemplary frame 510 is open along the top 512 and along one side (a front) 514, while it is closed along the other side (rear) and the ends. The substrate 520 includes an opening 522 that allows part of the handling system 500 to pass through as described below. For example, the opening 522 can be a circular shaped opening. When installed in the third section 400, the substrate 520 is supported by the frame 510.

Figure 3A:
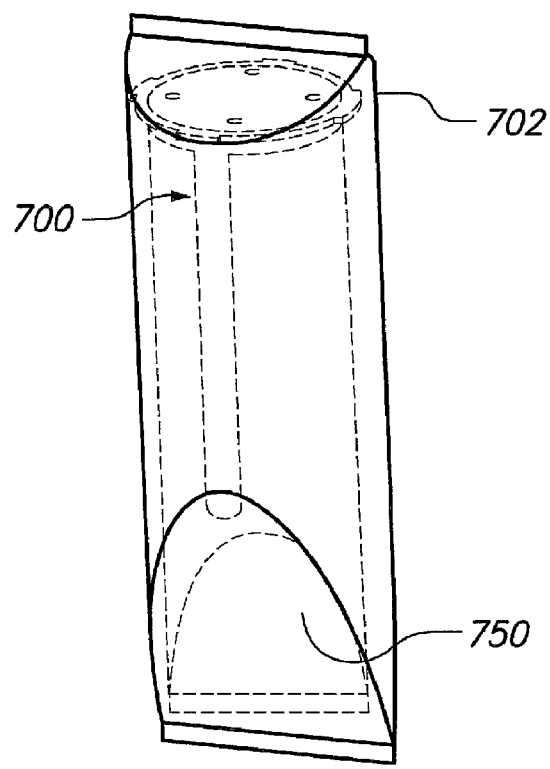
FIG. 3A is a perspective view of a disposable packaging sleeve for use in the bag handling system of FIG. 2 and shown prior to use.

The system 500 includes an automated bag sealing mechanism 600 that receives the items to be sealed in an enclosure and operates on the same to seal each item in an enclosure which is then delivered to a location, such as a bin, where it can be collected and then moved to another location, such as a point of use. Before describing in detail the bag sealing mechanism 600, a discussion of a disposable packaging sleeve 700 for use in the bag sealing mechanism is in order. FIG. 3A shows the packaging sleeve 700 contained within a sealed protective package 702 prior to its use and insertion into the mechanism 600. The protective package 702 protects the packaging sleeve 700 after its assembly, during storage and during transportation to a customer. The protective package 702 can be formed of a plastic sheet material that encloses the sleeve 700 and is sealed along all peripheral edges (sides and ends) thereof. When the customer is ready to use the sleeve 700, the customer simply removes the package 702 from the sleeve 700. For example and according to one embodiment, the package 702 can be an outside heat sealed bag that ensures that the package 702 is clean.

Figure 3B:
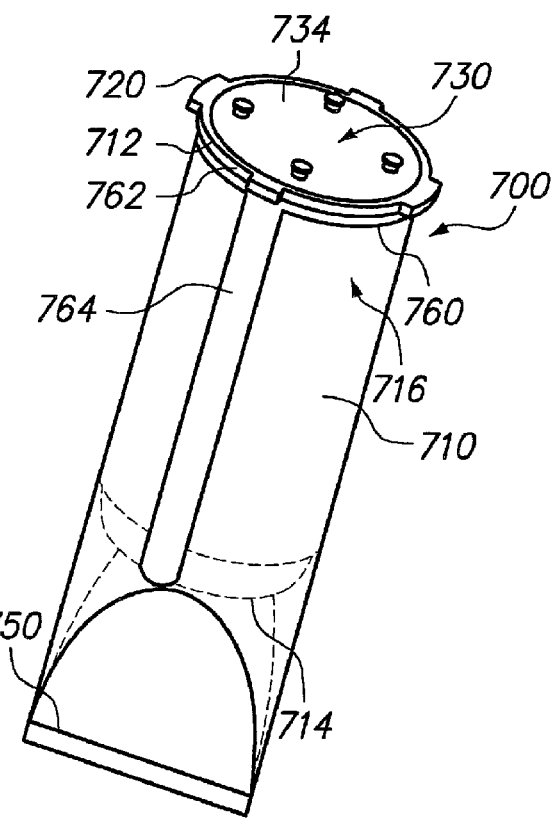
FIG. 3B is a perspective view of the sleeve of FIG. 3A with a protective outer packaging removed therefrom.

FIG. 3B shows the sleeve 700 with the outer packaging 702 having been removed. The sleeve 700 is formed of a number of different components and in particular, the sleeve 700 includes a sleeve body 710 that is a hollow elongated structure (e.g., a tube) that has an open first end 712 and an opposing open second end 714. The body 710 has an outer surface 716 and an opposing inner surface 718. At the open first end 712, at least one and preferably a plurality of locking tabs 720 are provided. The locking tabs 720 extend radially outward from the first end 712 and are formed circumferentially about the first end 712. As shown, there can be more than one type of locking tabs 720. The illustrated locking tabs 720 include two different types of locking tabs, namely, a small rectangular shaped locking tab and a large rectangular shaped locking tab.

Now referring to FIGS. 2-5 and 10, the sleeve 700 also includes a top removable cover 730 that is configured to lockingly engage and mate with the sleeve body 710 so as to seal the first end 712 thereof. As best shown in the exploded view of FIG. 4, the cover 730 is constructed to sealingly close off the first end 712 when it is inserted and locked to the first end 712. The illustrated cover 730 is a disk shaped member that has an inner surface that faces the interior chamber of the sleeve 700 when the cover 730 lockingly engages the sleeve body 710 and an opposite outer surface 734 that faces outward from the sleeve 710. The cover 730 also includes a peripheral side edge 735 that can include a seal element 701 (such as an O-ring) to allow the cover 730 to seal relative to the inner surface of the cover 730. The seal element 739 can be thought of as an upper seal due to its position closer toward the outer surface 734.

The peripheral side edge 735 also includes locking means for selectively locking the cover 730 to the sleeve body 710. For example, the side edge 735 can include a locking pin assembly that includes a locking pin 737 that extends radially outward therefrom through an opening that is formed in the peripheral side edge 735. The pin(s) 737 is configured to be received into a locking slot or channel 739 that is formed in the inner surface 718 of the sleeve body 710. The locking pin assembly also includes a biasing member (spring 740) that applies a biasing force to the pin 737 to cause the pin 737 to be extended into the locking channel 739 when the cover 730 is locked in place relative to the sleeve body 710. The cover 730 also includes a locking cam pin 742 that is received in a bore that is open along the outer surface 734. In particular, in the center of the cover 730 includes a bore that receives the cam pin 742 and intersects the bore that contains the pin 737 and biasing member 740. One end of the cam pin 742 is designed to engage and be coupled to the pin 737. Manipulation of the cam pin 742 causes the release of the pin 737 in that by manipulating the cam pin 742, the pin 737 can be placed in an unlock position which permits the biasing member 740 to release it energy. This results in the pin 737 being extended into the aligned locking channel 739 when the cover 730 is locked relative to the sleeve body 710.

The locking channel 739 has a first section (vertical section) that is formed along a length of the sleeve body 710 and a second section (horizontal section) that intersects the first section at one end thereof. The first and second channel sections thus generally are in an "L" shape. To lock the cover 730 to the sleeve body 710, the pins 737 are inserted into the locking channel 739 and by rotating the cover 730, the pins 737 are moved into a locking position in the channel 739 that prevents the cover 730 from being removed.

The outer surface 734 of the cover 730 includes locating and coupling members 732 that serve to couple the cover 730 to another member as described below. The coupling members 732 can be in the form of a plurality of circular shaped protrusions or upright posts that are spaced across and located in different locations. The protrusion 732 can have sections with varying diameters and in particular, a top (distal end) of the protrusion 732 can be in the form of a flange that has a greater diameter than a bottom portion.

In the locked position, the upper surface of the cover 730 is generally flush with the top edge (first end 712) of the sleeve body 710. The locking members 732 extend beyond the first end 712 of the sleeve body 710.

The sleeve 700 is designed to hold a length of a bag 750, such as a plastic bag, that receives an item and is sealed, as described below, at select locations resulting in the item being sealingly contained within the plastic bag. The bag 750 has a complementary shape to the sleeve body 710 and in particular, the bag 750 can be a tubular shaped bag. In one embodiment, about 14 to 20 feet of bag material is compressed and stored along the outer surface 716 of the body 710. For example, the bag material can be gathered and compressed linearly along the sleeve body 710, thereby along a large length of bag material to be stored along a much smaller length body 710. The bag material is typically a plastic material that has a selected, suitable thickness to allow items to be securely contained therein in a sealed manner. Typically, the bag material is transparent to allow viewing of the sealed item and allow any identifying indicia to be viewable.

The sleeve 700 also includes a bag holding element (bag tensioner) 760 that not only securely attaches one end of the bag 750 to the sleeve body 710 but also tensions the compressed bag 750 so as to meter how much bag material 750 is dispensed at one time (e.g., one pulling motion). Any number of different devices or mechanisms can serve as the bag tensioner 760 so long as they perform the intended function described herein.

For example and according to one embodiment, the bag tensioner 760 includes a top sealing ring 762 and a pair of elongated tensioning arms 764 that are each attached at one end to the top sealing ring 762. Due to the tubular, cylindrical shape of the sleeve body 710, the top sealing ring 762 has a circular shape (annular shape). When installed, the top sealing ring 762 is positioned proximate to or in an abutting relationship with the undersides of the locking tabs 720 at the first end 712. The bag 750 is thus positioned underneath the top sealing ring 762 against the sleeve body 710. The top sealing ring 762 thus sealingly attaches one end of the bag 500 to the outer surface of the sleeve body 710 near the first end 712. In effect, the bag 500 is pinched and sealed in place along the outer surface of the sleeve body 710. Various sealing techniques, including heat seals, can be used to seal the end of the bag 750 to the outer surface of the body 710.

In addition, it will be appreciated that the top sealing ring 762 can be formed as two parts that can be interlockingly attached to one another. Thus, the bag 750 can first be disposed about the outer surface of the sleeve body 710 and gathered (compressed) therealong and then the two parts of the ring 762 are disposed over the end of the bag 750 and are interlockingly engaged with one another.

The arms 764 are typically located opposite one another (180 degrees apart); however, the arms 764 can be disposed at other angles relative to one another. The length of the arms 764 is selected so that when the tensioner 760 is fully installed on the body 710, distal ends 765 of the arms 764 are proximate the open second end 714 of the sleeve body 710. It will be appreciated that the bag 750 in its compressed form is disposed underneath the arms 764. The arms 764 are thus tensioning elements that hold and maintain the compressed (gathered) bag 750 along the outer surface of the sleeve body 710. Accordingly, the arms 764 have some flexing action to accommodate the gathered bag 750; however, the natural biasing action of the arms 764 applies tension to the bag 750 such that when the exposed end of the bag 750 is pulled away from sleeve body 710, the bag 710 is slowly released from the second end 714 of the sleeve body 710.

The bag 750 can be provided with one end already sealed (e.g., a heat seal) and therefore, the placement of the bag 750 onto the sleeve body 710 only requires the opposite open end of the bag 750 to be disposed about the outer surface of the sleeve body 710 and then brought into position at the first end 712 of the sleeve body 710 where it is fixedly attached to the sleeve body 710. The insertion of the bag 750 onto the outer surface of the sleeve body 710 results in the second end 714 of the sleeve body 710 being closed.

In another embodiment, the bag tensioner 760 can be in the form of another sleeve which contacts the underlying bag and applies the necessary tension (force) to the bag so as to provide the desired metering of the bag.

The sleeve 700 includes a sleeve locking member 800 that selectively is placed in engagement with the sleeve body 710. As shown in FIG. 2, the sleeve locking member 800 is coupled to the substrate 520 and in particular, the sleeve locking member 800 is axially aligned with the opening 522 such that the interior bore formed therein is in registration with the opening 522. This permits an item that is inserted into the sleeve locking member 800 to pass directly into the sleeve body 710. As shown in FIG. 2, a spacer 801 can support the sleeve locking member 800 and space it from the top surface of the substrate 520. The spacer 801 can have an angled top surface which results in the sleeve locking member 800 being supported at an angle as illustrated. The spacer 801 can thus be a wedge shaped member that is inserted between the sleeve locking member 800 and the upper surface of the substrate 520.

The spacer 801 is an annular shaped member that is attached to the top surface of the substrate 520 with the central opening of the spacer 801 being axially aligned with the opening 522 to allow the item to pass through the sleeve locking member 800, the spacer 801 and then into the sleeve body 710. When the sleeve body 710 is attached to the sleeve locking member 800, the sleeve body 710 is in a vertical position with a majority of the sleeve body 710 being located below the substrate 520. The sealed second end 751 of the bag 750 (disposable packaging sleeve) is thus located below the substrate 520.

Figure 4:
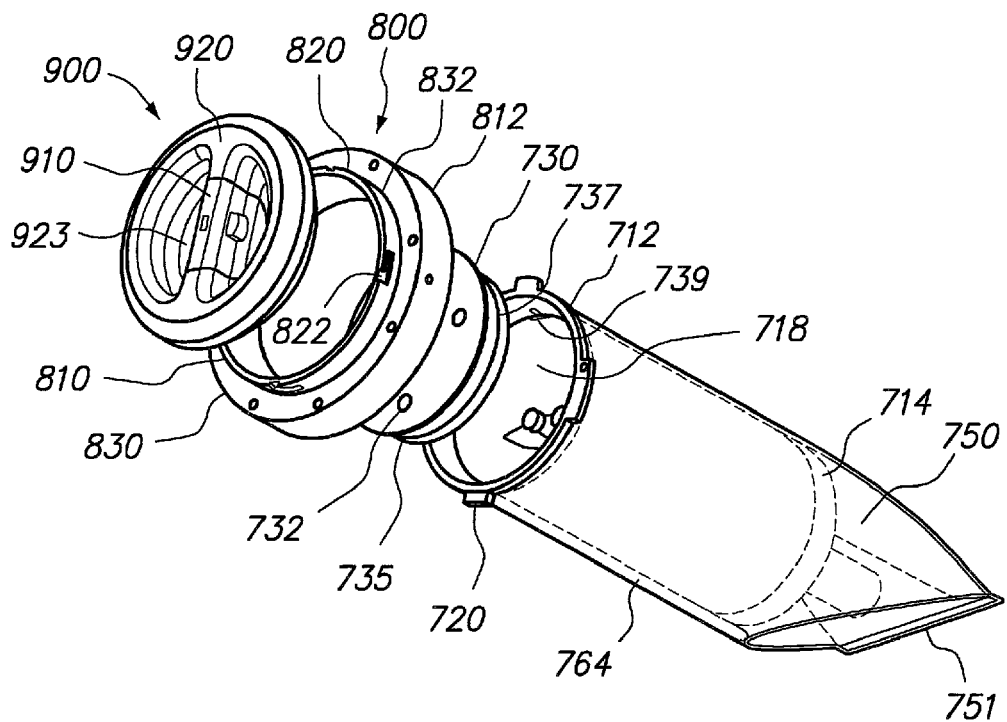
FIG. 4 is a perspective view of a docking ring cover and a top cover (cap) shown exploded from the sleeve.

The sleeve locking member 800 is an annular member that includes a top edge 810 and an opposite bottom edge 812. The locking member 800 includes an inner surface. As shown in FIG. 4, the locking member 800 can include two different parts, namely, a first part 820 and a second part 830. The first part 820 has a thinner construction than the second part 830 and therefore, a shoulder 832 is formed (e.g., a right angle shoulder). The first part 820 defines the top edge 810 and on an outer surface of the first part 820, a locking channel 822 is formed. The locking channel 822 is open along the top edge 810 and similar to the locking channel 739, the locking channel 822 is defined by two sections, namely, a first vertical section that is open along the top edge 810 and a second horizontal section that intersects and is open to the first section at the opposite end of the first section.

Figure 5:
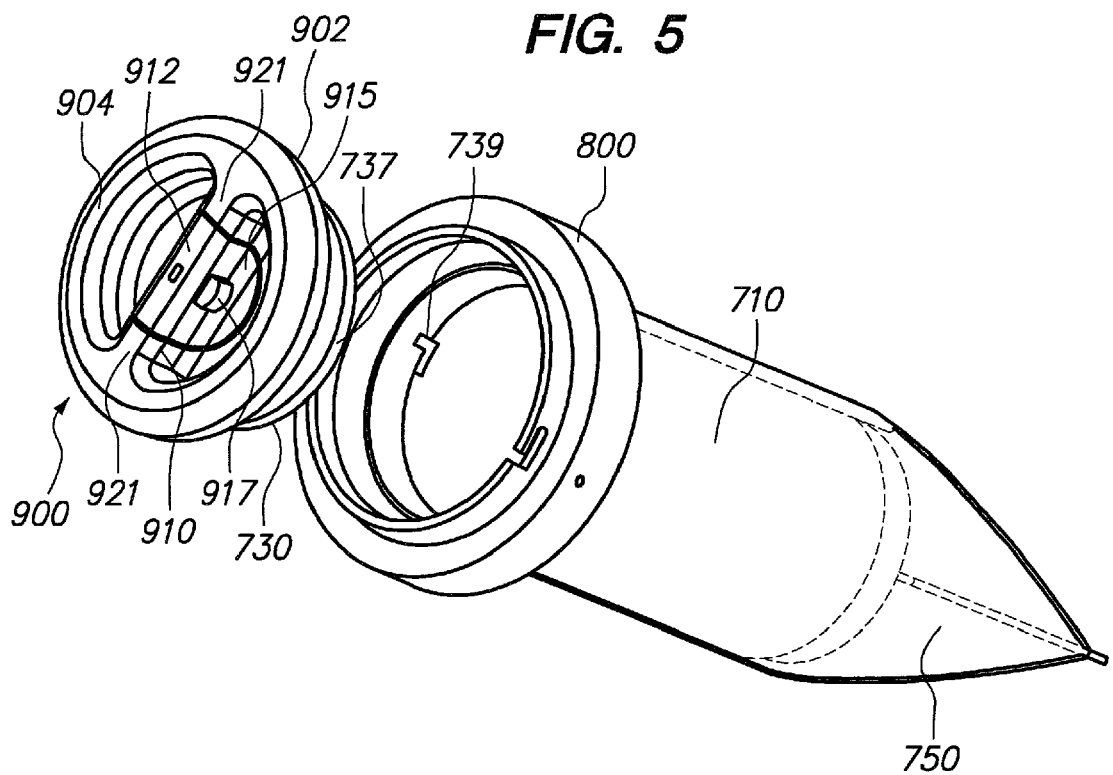
FIG. 5 is a perspective view of the docking ring cover attached to the cap and exploded from the sleeve.
Figure 6:
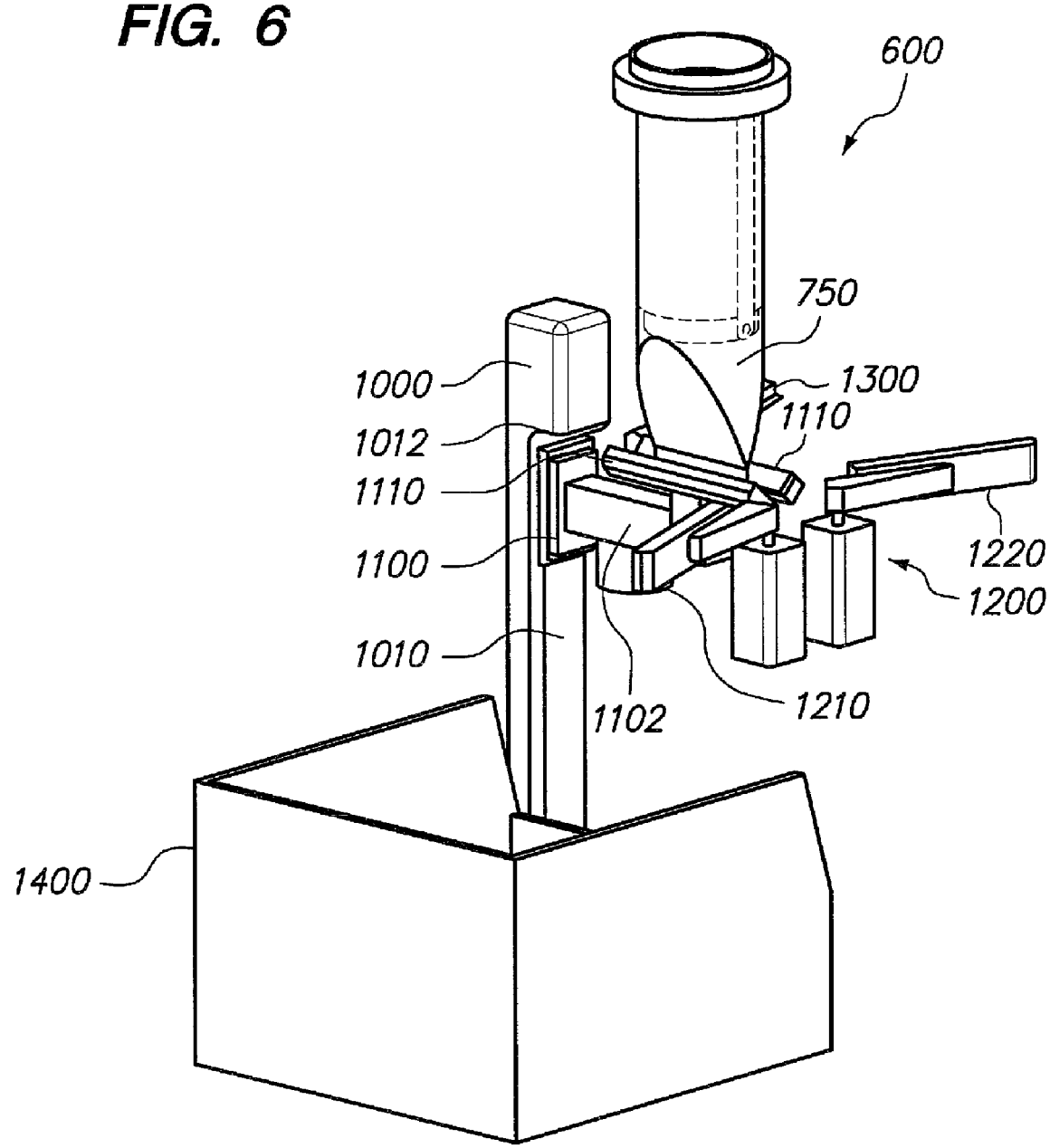
FIG. 6 is a perspective view of components of the bag handling system shown a heat sealer and cutter in retracted positions.
Figure 7:
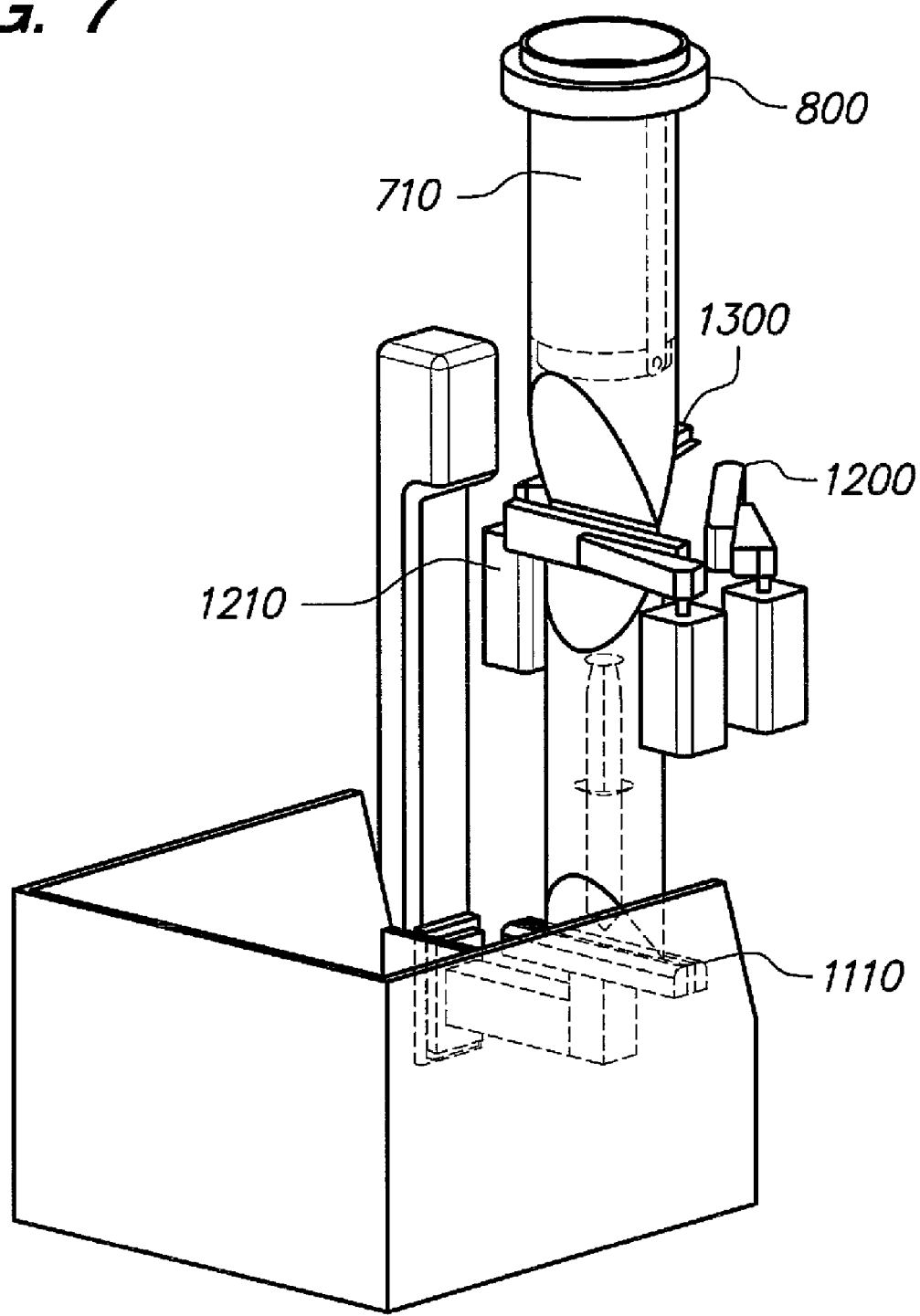
FIG. 7 is a perspective view of the bag handling system with a gripper device in a retracted position and the heat sealer in an intermediate position.
Figure 8:
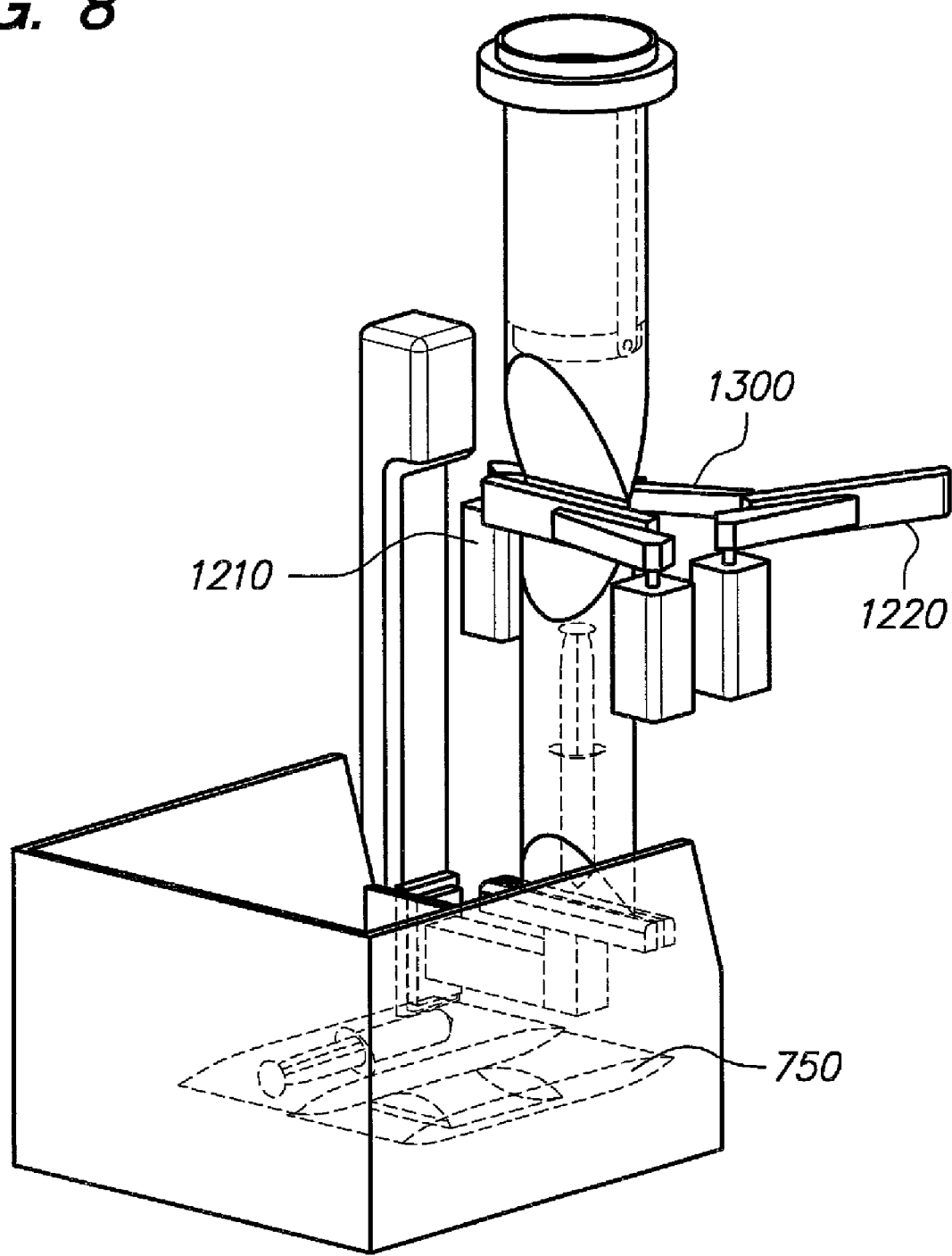
FIG. 8 is a perspective view of the bag handling system with a heat seal having been formed and the cutter in an intermediate position.
Figure 9:
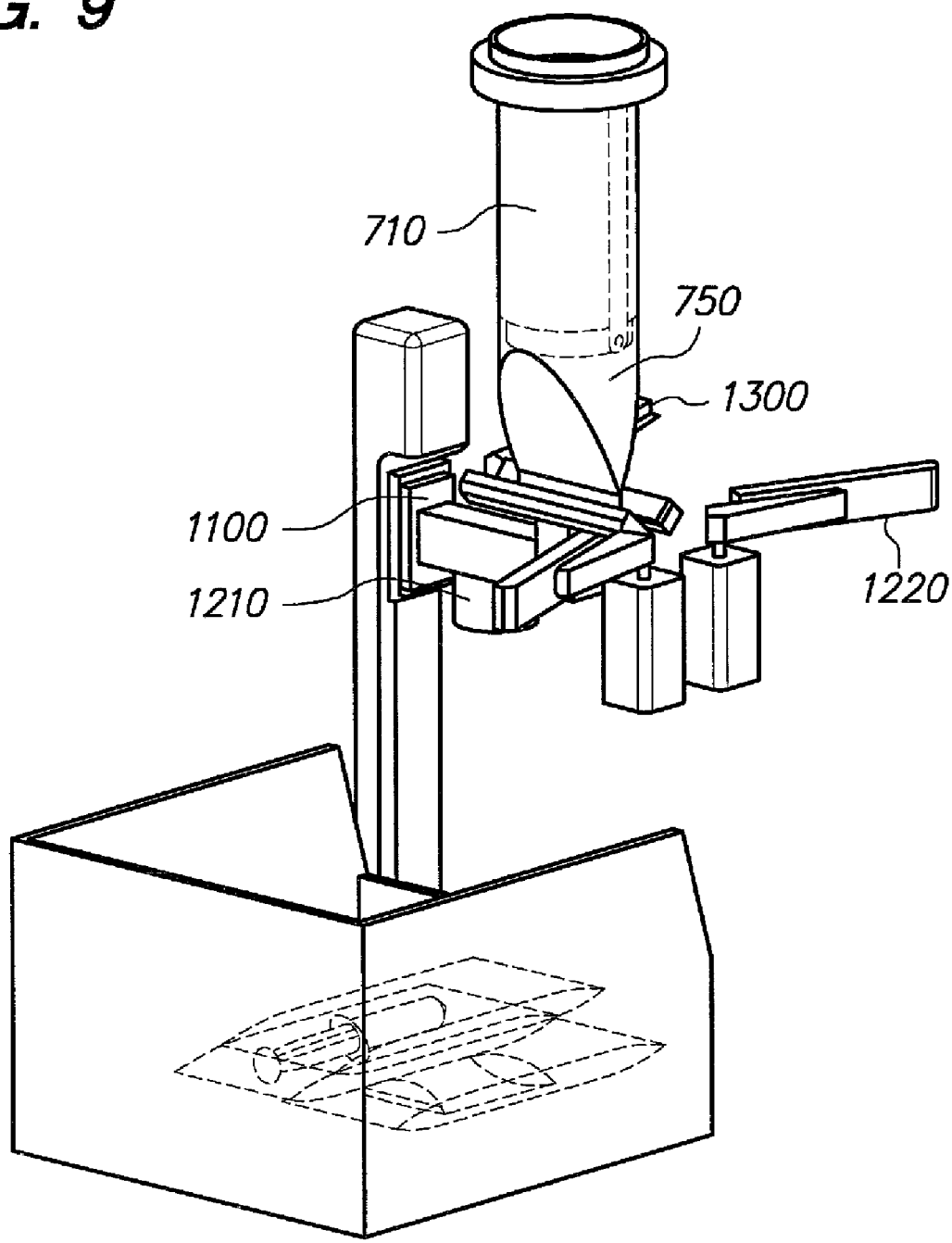
FIG. 9 is a perspective view of the bag handling system with a sealed enclosure being released into the collection bin and a next packaging sleeve being exposed for being extended.
Figure 10:
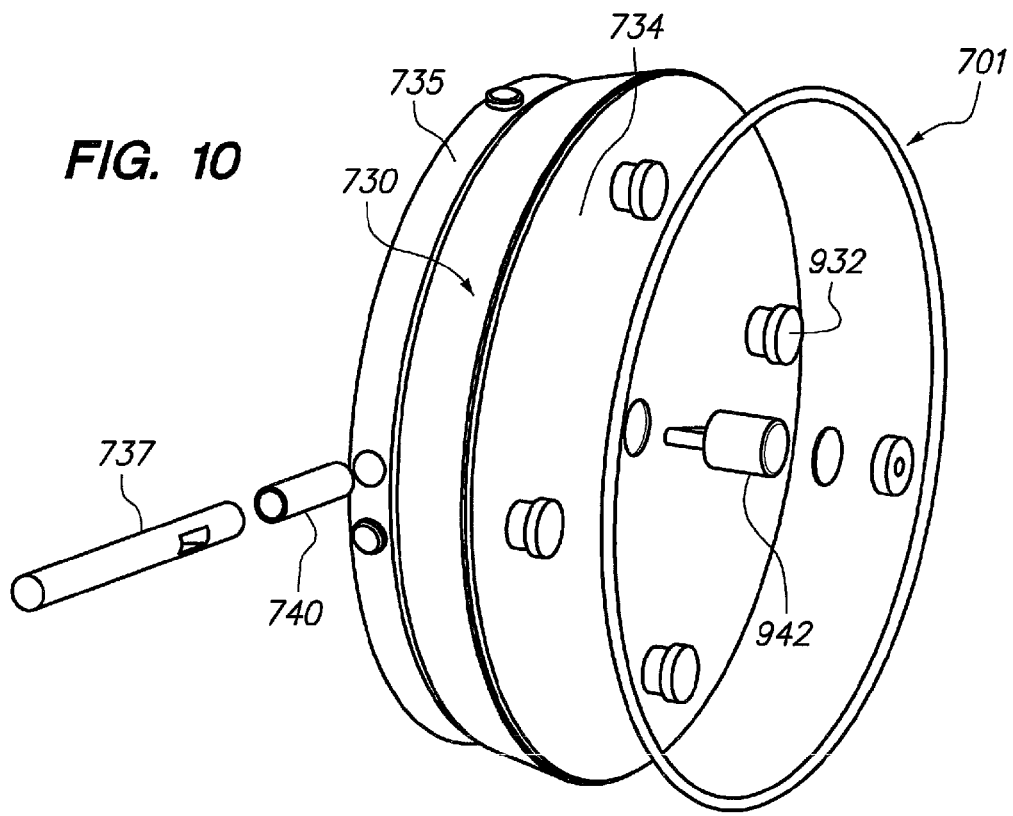
FIG. 10 is a perspective view of a the components that form the packaging sleeve top cover.

The sleeve locking member 800 includes locking features that are complementary to the locking tabs 720 to allow the sleeve locking member 800 to interlockingly engage the first end 712 of the sleeve body 710 as shown in FIG. 5. The inner diameter of the first part 820 is about equal to the inner diameter of the sleeve body 710 so that a smooth, substantially continuous inner surface results when the sleeve locking member 800 is securely attached to the sleeve body 710.

Figure 11:
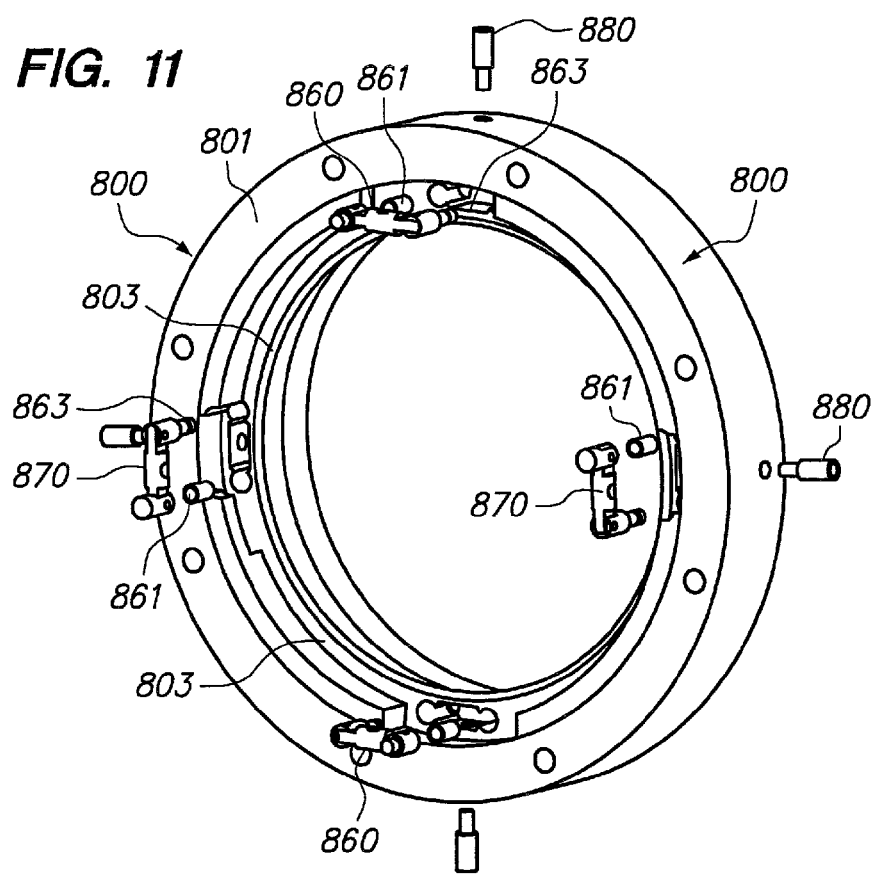
FIG. 11 is a rear perspective view of the sleeve locking member.

As shown in FIG. 11, the sleeve locking member 800 includes a bottom surface 801 and a bottom track (annular ring) 803 that provides a surface to which the top of the cover 730 seats against. The track 803 includes a number of cutouts that permit a degree of rotation of the locking tabs 720. Within the cutouts and circumferentially spaced along the track 803 a plurality of through holes or bore are formed for receiving a plurality of locking mechanisms. For example, the locking mechanism can include a plurality of first locking mechanism 860 for selectively locking the sleeve locking member 800 to the sleeve body 810 and a second locking mechanism 870 for selectively locking the sleeve locking member 800 to another member as described below. Each of the locking mechanisms 860, 870 includes a pivot pin 880 to permit movement thereof between an unlocked position and a locked position. The pivot pin 880 is received within a bore that is formed along an outer surface of the circumferential side of the member 800 and is operatively coupled to the respective locking mechanism. It will be appreciated that the locking mechanisms can be exposed along different surfaces of the member 800. For example, the first locking mechanism 860 can be accessible along a bottom face (surface) of the member 800, while the second locking mechanism 870 can be accessible along a top face (surface) of the member 800. In one embodiment, each locking mechanism includes a protrusion or post that protrudes outwardly from the respect top or bottom face of the member 800 and into engagement with a complementary locking feature to cause a coupling between the member 800 and the other member.

Each of the locking mechanisms 860, 870 can include a biasing element (spring) 861 that intimately and operatively are coupled to an internal locking assembly seal 863.

As described below, to lock the sleeve body 710 to the member 800, the first end of the sleeve body 710 is mated with the track 803 such that the locking tabs 720 are received into the cutouts formed along the track 803.

The sleeve 700 also includes a docking ring cover 900. The docking ring cover 900 is complementary to both the sleeve locking member 800 and the cover 730. The docking ring cover 900 includes a bottom surface 902 and an opposite top surface 904. The top surface 904 is designed as an area that can be grasped by the operator to allow the cover 900 to be picked up, etc.

Figure 12:
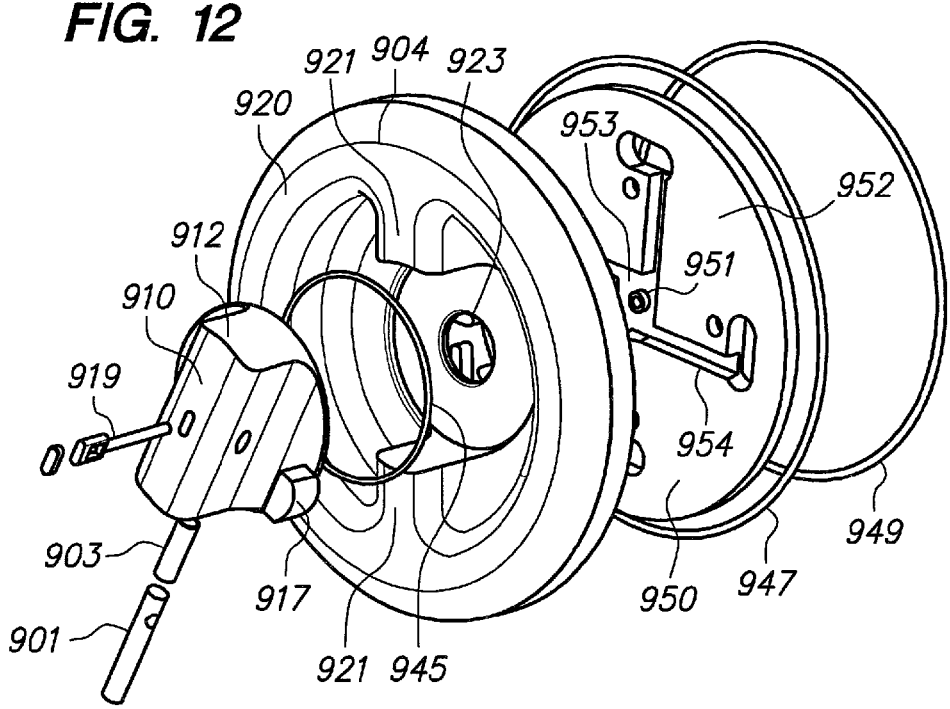
FIG. 12 is a top exploded perspective view of the docking ring cover.
Figure 13:
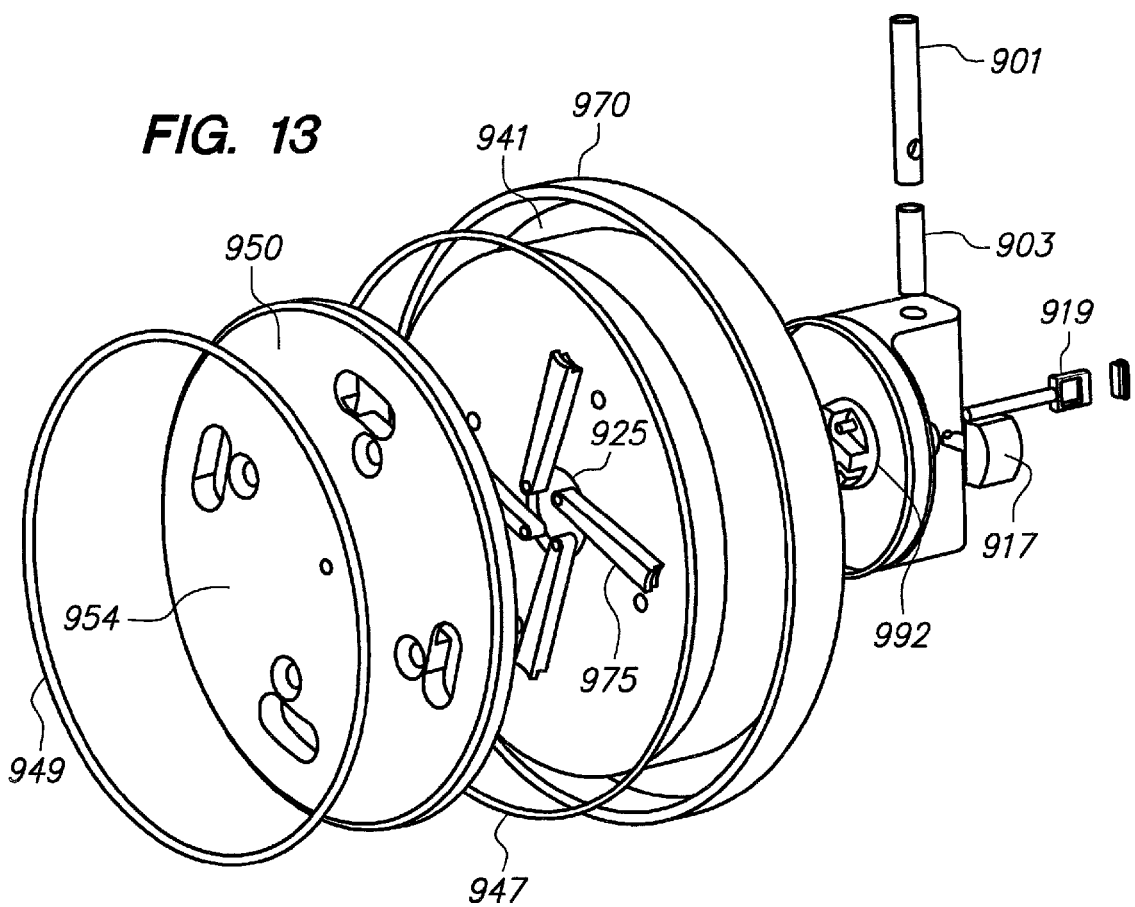
FIG. 13 is a rear exploded perspective view of the docking ring cover.

As best shown in FIGS. 12 and 13, the docking ring cover 900 is actually formed of a number of parts that cooperate with one another. For example, the cover 900 includes a rotatable inner knob member 910, a main cover 920 and a back plate 950, as well as a number of seal elements (e.g., a first seal 945, a second seal 947, and a third seal 949). The inner knob member 910 is rotatable relative to the main cover 920 and the back plate 950. In the illustrated embodiment, the top surface 904 has a pair of recessed sections to allow insertion of the fingers of an operator and to permit the inner knob member 910 to be grasped and rotated relative to the main cover 920. The main cover 920 is a disk shaped member that includes a hollow interior cavity or compartment and has a central recessed section 923 that defines a floor and includes an opening 925 passing therethrough. The recessed section 923 includes an annular groove that receives the first seal 945. The first seal 945 is thus a seal ring for the inner knob member 910. A portion of the inner knob member 910 is received within the opening 925 of the floor 923 and is rotatable therein and therefore, the inner knob member 910 is also disk shaped.

The two recessed sections are defined in part by a pair of inward protrusions 921 that extends radially inward toward one another. The two protrusions 921 are located about 180 degrees from one another so as to be linearly aligned along lengths thereof.

The main cover 920 includes an outer flange 970 that defines the outer perimeter of the main cover 920 and a bottom surface 972. The opening 925 passes through the bottom surface 972. Along the bottom surface 972, the main cover 920 includes a number of movable locking arms 975. For example, each locking arm 975 is in the form of an elongated arm that includes a first end 977 and a second end 979 that includes a through hole formed therein. The second ends 979 are positioned within the opening 925. Accordingly, there are four ends 979 that are located in the opening 925. The first end 977 can be contoured, such as having an arcuate shape (e.g., concave). The second seal 947 is in the form of an under lid seal top cover that is disposed in an annular shaped groove 941 that is formed in the underside of the flange 970.

The back plate 950 is a disk shaped member that includes a first surface (top surface) 952 and a second surface (rear surface) 954. Each of the first and second surfaces 952, 954 has a number of surface features to permit coupling between the components of the docking ring cover 900. For example, the first surface 952 has a number of recessed channels formed therein and in particular, the first surface 952 can have a central recessed section 953 and there are a plurality of channels 954 that are open at one end to the recessed section 953 and extend outwardly therefrom. The channels 954 can be linear in nature. The back plate 950 also includes a number of through openings (e.g. oval shaped apertures) 990 that are formed therein. At an opposite end, the channel 954 is in communication with the opening 990. In other words, one end of the channel 954 is in communication with the recessed section 953, while the opposite end is in communication with the opening 990. A protrusion or nub 951 is formed within the recessed section 953. The second surface 954 includes a number of recessed portions. For example, the second surface 954 can include a plurality of circular shaped recesses 955. The third ring 949 is received within an annular groove that is formed around the periphery of the back plate 950.

The main cover 920 and the back plate 950 are constructed to mate with each other. The first surface 952 faces and engages the bottom surface 972. The locking arms 975 are received within the channels 954. Additional details of this coupling are discussed below.

The inner knob member 910 has a central upright bridge portion 912 that extends across a width of the knob member 910 and extends upwardly from a floor or base 915 of the knob member 910. Within the bridge portion 912, a longitudinal bore is formed that receives an inner locking knob pin 901 and a biasing element 903, such as a spring. The bridge portion 912 also includes a button (slide pin) 917, which as described hereinafter, is used to disengage the cover 730 from the body sleeve 710. The button 917 is in the form of a slide pin that is received in a bore formed in the bridge portion 912 at a right angle to the longitudinal bore. When the slide pin 917 engages the pin 901 (e.g., a distal end of the pin 917 being received into an opening formed along the pin 901. A release pin 919 is received within an opening formed in the top surface of the bridge portion 912. The release pin 919 is in communication with the locking pin 901/biasing element 903 assembly and is designed so that once the pin 919 is removed, the locking mechanism can be operated.

Figure 14:
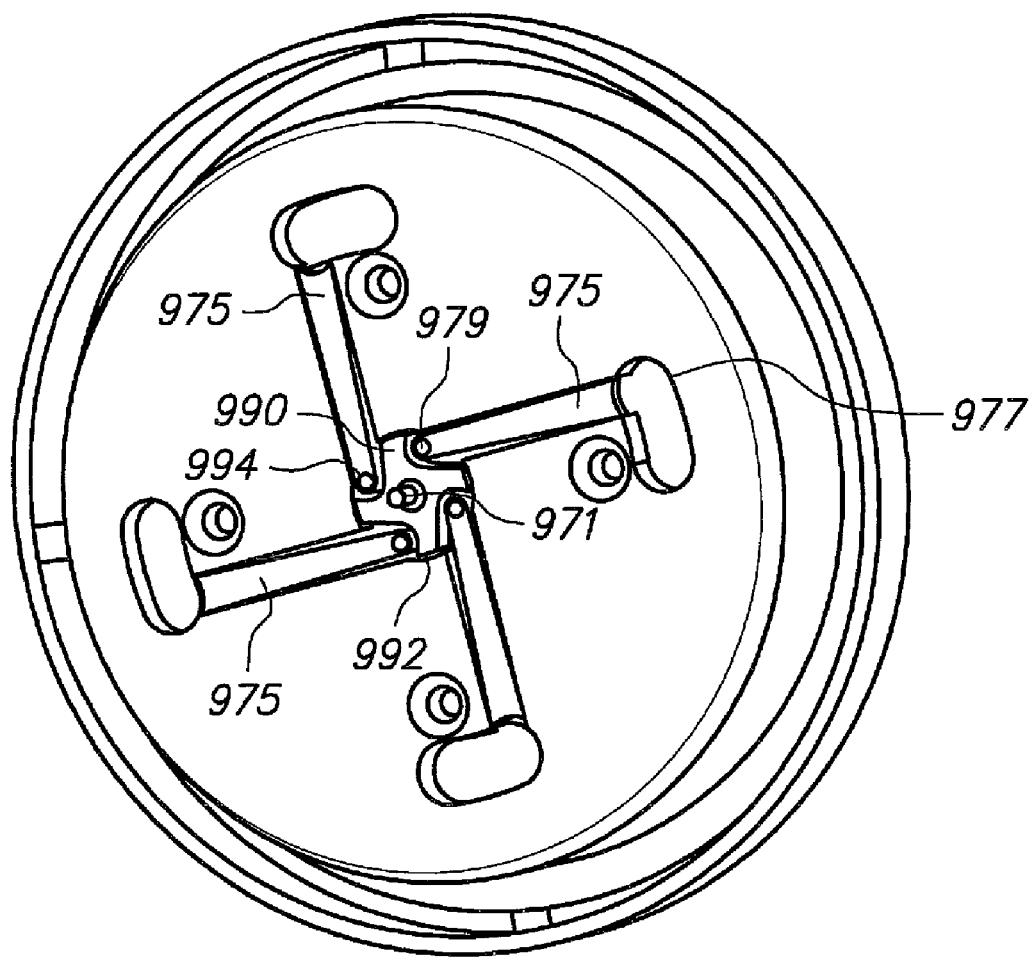
FIG. 14 is a rear perspective view of the docking ring cover in a locked position with a back plate thereof being transparent to allow view of the inner components.

An underside of the inner knob member 910 includes a shaped boss or protrusion 990 that has a circular side wall that is shaped and sized to be received within the opening 925. The protrusion 990 also includes a plurality of fingers or spokes 992. Each finger 992 has curved side walls and in particular and as shown in FIG. 14, adjacent fingers 992 define a sloped surface (cam surface) and between adjacent fingers 992, a pin or post is shown 994. In addition, the protrusion includes a center pin 971 that extends outwardly therefrom. When the cover 900 is mated with the top cover 730, the pin 994 engages the cam pin 742 to cause activation of the locking mechanism of the cover 730. The pin 995 is received within the opening formed in the second end 979 of the arm 975 which results in the arm 975 being coupled to the protrusion 990. When the inner knob member 910 is rotated, the rotation of the protrusion 990 causes movement of the arms 975 within the channels 954.

FIG. 14 shows the interlocking arms 975 in retracted positions which corresponds to the unlocked position of the inner knob member 910. When the inner knob 910 is rotated as described below, the arms 975 are moved longitudinally within the channels 954 so that the first end 977 is moved into the opening 990. In FIG. 14, the rear backing plate 950 is transparent in order to permit viewing of the locking arms 975 in the locked positions.

FIG. 2 shows the bag or packaging sleeve 750 installed onto the sleeve assembly (locking member 800). Once the bag 750 is installed onto the sleeve assembly, then the docking ring cover 900 can be removed for access to the interior of the packaging sleeve 750 (bag).

Once the packaging sleeve body 710 is installed onto the locking member 800, the locking tabs 720 are received into the cutouts that are formed in the track formed on the underside of the locking member 800. Some of the locking tabs 720 engage the first locking mechanisms 860 and in particular, the loading of the sleeve body 710 applies a force to the first locking mechanism 860 resulting in the locks on the top cover 730 being released. It will also be appreciated that there are two locking assemblies for both interlocking systems. Once the packaging sleeve 710 is inserted, the interlocks are released for the top cover 730 but the packaging sleeve 710 must then be rotated into the correct docking position for the top cover 730 to engage the interlocks (locking assemblies) for the packaging sleeve. If this is not done, the top cover 730 will not come off and the packaging sleeve will dock. Once the packaging sleeve 710 has been rotated to the docking position, the interlocking mechanism of the docking ring cover 900 can be engaged to the top cover 730 by actuation of their respecting locking mechanisms. In particular, the inner knob 910 is rotated from the unlocked position where it does not align with the protrusions to a locked position, where the inner locking knob 910 axially aligned with the protrusions of the main cover 920, resulting in the locking arms being moved to their extended positions and into contact with the top cover 730.

Once all inner cover (cover 730) to docking ring cover 900 is complete, the user can now rotate the docking ring cover 900 to intimately contact the interlocks for the packaging sleeve 710 and thereby permit removal of the two covers 730, 900 together. It will be appreciated that when the covers 730, 900 are locked together, the bottom seal of the cover 900 engages (seals) with the top seal of the packaging sleeve cover 730.

Thus, in one embodiment, to open the docking ring cover 900 and remove the cover 730 the following steps are undertaken. The release pin that is part of the inner knob member 910 is pressed. Next, the inner knob member 910 is rotated until it stops. The slide pin is slid to a locked position whereby the inner knob member 910 is securely coupled to the cover 730 and therefore, the cover 730 is lockingly coupled to the ring cover 900. In the locked position, the inner knob member 910 is not linearly aligned with the protrusions 921 but rather is offset therefrom. The rotation of the inner knob member 910 causes rotation of the cover 730 and in particular, causes the pins 737 of the cover 730 to disengage from the locked position and move to a position where the pins 737 can be disengaged from the corresponding locking channels 739. The docking ring cover 900 is further rotated and this allows the cover 730 to be removed from the sleeve body 710 by lifting of the attached docking ring cover 900 and the cover 730.

Once the covers 730, 900 are locked together and removed from the docking ring assembly, the disposable sleeve (bag) 750 is now locked to the docking ring assembly and will not be able to be removed from the docking ring assembly. In other words, the sleeve body 710 is in a locked position relative to the sleeve locking member 800 and therefore, the sleeve body 710 cannot be pulled from or otherwise easily removed from the sleeve locking member 800. More particularly, the locking tabs 720 remain in a locked position with respect to the sleeve locking member 800, thereby preventing separation of the sleeve body 710 from the sleeve locking member 800.

Referring to FIGS. 2 and 6-9, as previously mentioned, the automated bag sealing mechanism 600 is at least partially automated and is configured to receive and seal an item within the material of the bag (protective sleeve) 750. The mechanism 600 includes a support post (e.g., vertical or inclined) 1000 that includes a guide track 1010 formed along a length thereof. The post 1000 can also include at least one stop 1012 that is designed to limit the travel of an object within the guide track 1010 along the length of the post 1000.

A robotic arm 1100 is coupled to and driven along the guide track 1010 and is configured to perform certain bag handling and processing operations. For example, the robotic arm 1100 can include a horizontal support member 1102 that extends radially outwardly from post 1000 and is preferably coupled to the guide track 1010 at a right angle. A free distal end of the member 1102 includes a pair of controlled grippers (gripping elements) 1110 that can be controlled and moved between an open position in which an item, such as the bag 750, can be placed between the grippers 1110 and a closed position in which the grippers 1110 are closed and the item between the grippers 1110 is securely grasped and held therebetween. In the illustrated embodiment, each gripper 1110 is an elongated bar like member that has an inner surface that faces the other gripper 1110. The inner surface is a contact or grip surface that engages the bag 750. The inner surface can be modified (i.e., roughened) to enhance the gripping characteristics. For example, the inner surface can be a rubber pad or the like. The grippers 1110 can pivot or move linearly between the open and closed positions.

Any number of different means can be used to drive the robotic arm 1100 in a controlled manner where the location of the robotic arm 1100 can be precisely monitored and regulated. For example, a stepper motor can be used to drive the robotic arm 1100 vertically along a length of the guide track 1010. Since the motor's position can be precisely controlled, a correlation can be made between the number of steps undertaken by the motor and the distance the robotic arm 1100 has been driven. This permits precise control over the location of the robotic arm 1100 along the guide track 1010.

As explained below, the grippers 1110 are intended to grasp the sealed end of the bag (protective sleeve) and linear movement of the robotic arm 1100 is translated into an unfurling action whereby the bag 750 is slowly released from the sleeve body 710. The tensioning elements (arms) 764 cause a controlled unfurling of the bag 750 from the sleeve body 710 as discussed above. Accordingly, a length of bag material that is unfurled can be easily calculated since the position (a first position or upper position) of where the grippers 1110 grasp the bag 750 is known and the end position of the grippers 1110 after the robotic arm 1100 has been driven to a second position.

The sealing mechanism 600 also includes a number of components that seal the bag 750 at select locations and also cut the bag 750 at a select location. More specifically, a heat sealer 1200 is provided for sealing the bag 750 at a specific location. In the illustrated embodiment, the heat sealer 1200 has a first part 1210 and a second part 1220, each of which is placed into contact with the bag 750 for heat sealing thereof. At least one of the first and second parts 1210, 1220 is heated to allow for the local sealing of the bag 750. In one embodiment, the first part 1210 is a support member that is not heated and the second part 1220 is heated. The first part 1210 is placed against and across one face of the bag 750 and the second part 1220 is placed against and across the opposite face of the bag 750.

The first and second parts 1210, 1220 are movable between an engaged position where the respective parts 1210, 1220 are placed in contact with the opposite faces of the bag 750 and an open position where the parts 1210, 1220 are spaced from and not in contact with the bag 750. In the illustrated embodiment, each of the first parts 1210, 1220 is operatively connected to a shaft that is driven (e.g., rotated) by a motor. When actuated, the motors cause the shaft to rotate and depending upon the direction of rotation, the parts 1210, 1220 are either driven toward one another into contact with the opposite faces of the bag 750 or they are driven away from one another, thereby being removed from contact with the bag 750. The parts 1210, 1220 can be driven independent from one another or they can be driven at the same time. The motion of the parts 1210, 1220 is similar to a wiping action.

In one exemplary heat sealing operation, the second part 1220, which is not heated, is first driven to its engaged position. This driving action results in the second part 1220 being placed into contact with the bag 750 (see FIG. 7). The second part 1220 is maintained in this engaged position, thereby applying an inward force to the bag 750. Next, the second part 1220 is then manipulated (driven) to its engaged position and as it is driven into engagement with the opposite face of the bag 750, the heat element of the second part 1220 engages the bag 750. This results in the bag 750 being captured and compressed (pinched) between the two parts 1210, 1220 and a heat seal is formed in the bag 750. Since the first and second parts 1210, 1220 are elongated horizontal structures, the heat seal is a linear seal that extends horizontally across the bag 750. In one embodiment, the heat seal actually consists of two distinct heat seals that are spaced from one another with an unsealed area therebetween.

The sealing mechanism 600 also includes a cutting element (cutter) 1300 that has a blade or the like for cutting the bag 750 at a specific location. The cutting element 1300 can be a linear blade 1302 that is horizontally oriented so that the bag 750 is cut horizontally across its width. Similar to the first and second parts 1210, 1220, the cutting element 1300 can be moved between different positions. More specifically, the cutting element 1300 can be moved between an engaged position where the cutting element 1300 is placed in contact with one face of the bag 750 (e.g., the face that the second part 1220 has contacted) and an open position where the cutting element 1300 is spaced from and not in contact with the bag 750. In the illustrated embodiment, the cutting element 1300 is operatively connected to a shaft that is driven (e.g., rotated) by a motor. When actuated, the motor causes the shaft 1310 to rotate and depending upon the direction of rotation, the cutting element 1300 is either driven toward the bag 750 or is driven away from the bag 750, thereby being removed from contact with the bag 750 (see FIG. 8). As with the motion of the parts 1210, 1220, the action of the cutting element 1300 follows a wiping action.

As shown, the cutting element 1300 and second part 1220 can be disposed on the same side of the bag 750, while the first part 1210 is located on the other side of the bag 750. The paths of the cutting element 1300 and the second part 1220 at least partially overlap and therefore, both components can not engage the bag 750 at the same time.

The location of the cutting element 1300 and in particular, the blade 1302 relative to the heat element of the second part 1220 is selected so that bag 750 is cut within the unsealed space that is formed between the two heat sealed region. In other words, the bag 750 is cut at a location that results in the bag material being sealed above the cut line and sealed below the cut line.

The normal operating procedure is that after the second part 1220 has engaged and heat sealed the bag 750 and is then moved to its open position, the cutting element 1300 is then moved into its engaged position. This action results in the sharp blade 1302 being driven into contact with the bag 750 resulting in the bag 750 being cut. Since the first part 1210 remains in the engaged position, the first part 1210 provides a solid substrate against which the bag 750 and the cutting element 1300 can be driven with force against the bag 750 to cause a shearing of the bag 750. The cutting element 1300 is then moved back to the open position and the second part 1220 is driven to its open position by driving the shaft in an opposite direction causing disengagement of the second part 1220 from the bag 750. At this point, the bottom sealed end of the bag 750 remains held between the grippers at one thereof and the top sealed end is free and folds over and is directed towards a collection or storage bin 1400. The grippers 1110 are then opened (e.g., pivoted open) and the bag 750 falls into the storage bin 1400 where it is collected (se FIG. 9).

Once the sealed bag 750 which contains an item, such as a drug filled syringe, a container, waste (such as contaminated wires, etc.) or replaced/serviced parts, etc., is disposed within the storage bin 1400, the steps of the bag sealing action are repeated. In particular, the loose sealed end of the bag 750 (defined by the section of the heat seal that was located above the cut line) is captured by the grippers 1110 when they are driven to their up position. The grippers 1110 are then closed to capture the sealed bottom end of the bag 750 and then the robotic arm 1100 is driven downward to a bottom position (the precise location can depend on the size of the item) that is to be inserted into the bag 750. For example, if a larger item is to be inserted into the bag 750, a greater length of bag material needs to be unfurled from the sleeve body 710.

The item is only inserted when the sealed end of the bag 750 is captured between the grippers 1110 and the robotic arm and grippers 1110 are in the bottom extended position (i.e., a length of bag material has been unfurled). After insertion of the item, the heat sealing and cutting processes proceed as described above.

It will also be appreciated that the bag 750 can be designed so that it provides ability to hang a dose without removing the over wrap completely. For example, the bag 750 can have a sealed opening that allows the bag 750 to be hung. In addition, the bag material is non-permeable to the drug or other hazardous contents located therein.

The robotic arm 1100 and other operative parts of the automated system are in communication with a controller (processor) that is part of a computer system that includes software that has executable code that controls the actions of the robotic arm 1100, the grippers 1110, etc. For example, an operator input can be provided for entering information such as the type and/or size of the item that is being inserted into the open end of the packaging sleeve for sealed enclosure therein. Based on this information, the controller can determine the distance that the robotic arm 100 needs to travel along the guide track 1010 in order to unfurl the proper length of bag material and thereby provide an adequate interior space in the bag 750 for containing the item and allowing the heat seal and cut line to be formed above the item. For example, the operator can input that the item being inserted is an IV bag and can even input a size of the IV bag or that it is a particular type of syringe; drug vial; etc.

In addition, once the sealing mechanism 600 has determined that the packaging sleeve body 710 contains the last bag (protective sleeve) 750, the operator is signaled (alerted) or otherwise warned that the disposable sleeve 700 needs to be replaced. The signal can be in the form of an audible or visual alarm or indicator, or a combination thereof. In other words, the sealed second end of the bag 750 that is captured by the grippers 1110 should not be pulled (unfurled) in a direction away from the first end 712 of the sleeve body 710 since no additional length of bag material is left to be unfurled and this could result in the sealed, attached first end of the bag 750 being detached from the first end of the sleeve body 710. This would result in a potentially hazardous situation since the sealed environment of the sleeve body 710 and the third section 400 of the system is destroyed. The operator is thus exposed to contaminants, such as cytotoxin drug particles, that may be present along the inner surface of the sleeve body 710.

When the sleeve 700 needs to be replaced, the covers 900, 730 need to be reinstalled so that the finished packaging sleeve 700 can be removed and disposed of. First, the button 917 on the side of the docking ring cover 900 is pressed. This resets the lock for the disposable sleeve top cover 730. Second, the combined docking ring cover 900 and the disposable top cover 730 are re-installed by placing the combined cover 900 and top cover 730 back onto the sleeve locking member 800 and then rotating the docking ring cover 900 to re-install both covers 900, 730 onto the sleeve locking member 800 and the sleeve body 710. The button 917 is then slid to the unlock position on the inner knob 910. This will unlock the inner knob 910 of the docking ring cover 900. Next, the inner knob 910 of the docking ring cover 900 is rotated to the un-lock position. Once these covers 900, 730 are unlocked, the disposable packaging sleeve 710 is unlocked and can be removed from the docking ring assembly. After removal of the sleeve body 710, a new sleeve body 710 can be inserted and locked in place using the procedure previously discussed herein.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. An apparatus for sealing prepared medications in enclosures comprising:
   a frame defining a first sealed space;
   a tubular sleeve having an open first end that is in selective communication with the first sealed space, an open second end, and an outer surface;
   a tensioner device that is disposed about an outer surface of the tubular sleeve for applying tension to a member disposed thereunderneath and configured to receive the prepared medication;
   a sleeve locking member that is coupled to the frame for releasably locking the tubular sleeve thereto the sleeve locking member when the first and second locking members engage one another, the sleeve locking member being constructed to permit the open first end of the tubular sleeve to be exposed to the sealed space; and
   a cap that is releasably attached to the first end of the tubular sleeve for sealing the first end, wherein the cap is constructed such that it cannot be removed until the tubular sleeve and the sleeve locking member are in a locked position where the tubular sleeve is sealed relative to the first space.

2. The apparatus of claim 1, further including a robotic gripper that moves along a guide track, the robotic gripper including a pair of grippers that are actuatable and move between an open position in which the packaging sleeve can be received between the grippers and a closed position in which the packaging sleeve can be captured between the grippers and a prescribed liner movement of the robotic gripper causing a predetermined length of the packaging sleeve to be unfurled from the tubular sleeve.

3. The apparatus of claim 1, further including a controller that calculates a length of the packaging sleeve that has been removed and a length of the packaging sleeve that remains on the tubular sleeve.

4. The apparatus of claim 1, further including an automated heat sealer that includes a first part and a second part, wherein at least one of the first and second parts includes a heated element that forms a heat seal in the packaging sleeve resulting in the prepared medication being sealed in the packaging sleeve.

5. The apparatus of claim 3, further including an automated cutter that includes a blade for cutting the sealed packaging sleeve within and along the heat seal, wherein the first part serves as a back support surface onto which the packaging sleeve is compressed by both the second part that contains the heated element and the blade during a cutting action after the heat seal has been formed.

6. The apparatus of claim 1, wherein the packaging sleeve is constructed to be hung on a support without removing a protective outer wrap and is formed of a material that is non permeable to the medication.

7. The apparatus of claim 1, further including a controller which is configured to calculate a length of the packaging sleeve that has been unfurled and send an alert when only a prescribed length of packaging sleeve remains unfurled.

8. The apparatus of claim 1, further including a dose collection bin for receiving the enclosed medications and a controller that is configured to send an alert signal when a predetermined quantity of enclosed medications are contained in the dose collection bin.

9. The apparatus of claim 1, wherein the member disposed underneath the tensioner device comprises a length of a flexible packaging sleeve that is open at one end and has an open interior space, the packaging sleeve being disposed about the outer surface of the tubular sleeve in a compressed form, the open end of the sleeve being sealingly attached to the first end of the tubular sleeve, wherein the tensioner device applies tension to the packaging sleeve to control the unfurling thereof from the tubular sleeve.

* * * * *